United States Patent [19]

Tsilibary et al.

[11] Patent Number: 5,242,826
[45] Date of Patent: * Sep. 7, 1993

[54] POLYPEPTIDES FOR ADHERING CELLS TO A SUBSTRATE

[75] Inventors: Effie C. Tsilibary; Leo T. Furcht, both of Minneapolis, Minn.

[73] Assignee: Regents of the University of Minnesota, Minneapolis, Minn.

[ * ] Notice: The portion of the term of this patent subsequent to Oct. 24, 2006 has been disclaimed.

[21] Appl. No.: 705,086

[22] Filed: May 24, 1991

Related U.S. Application Data

[62] Division of Ser. No. 648,190, Jan. 31, 1991, Pat. No. 5,059,425, which is a division of Ser. No. 397,012, Aug. 22, 1989, Pat. No. 5,007,925, which is a division of Ser. No. 106,858, Oct. 8, 1987, Pat. No. 4,876,332.

[51] Int. Cl.$^5$ .................. C12M 3/00; C12N 11/02; C12N 5/00; A61K 37/02
[52] U.S. Cl. .................. 435/287; 435/177; 435/181; 435/240.23; 435/240.242; 435/240.243; 530/326; 530/327
[58] Field of Search ............... 530/326, 356; 424/443, 424/444, 445, 446, 447; 514/834, 801, 773; 435/174, 177, 181, 240.23, 240.24, 240.241, 240.242, 240.243, 287

[56] References Cited

U.S. PATENT DOCUMENTS

| | | | |
|---|---|---|---|
| 4,511,653 | 4/1985 | Play et al. | 435/69 |
| 4,578,079 | 3/1986 | Ruoslahti et al. | 623/11 |
| 4,591,456 | 5/1986 | Huc et al. | 530/356 |
| 4,677,058 | 6/1987 | Tryggvason et al. | 435/7 |
| 4,746,729 | 5/1988 | Kuettner et al. | 530/353 |
| 4,876,332 | 10/1989 | Tsilibary et al. | 530/326 |
| 5,007,925 | 4/1991 | Tsilibary et al. | 623/1 |
| 5,059,425 | 10/1991 | Tsilibary et al. | 424/445 |

FOREIGN PATENT DOCUMENTS

2059991 4/1981 United Kingdom .

OTHER PUBLICATIONS

K. Kuehn et al., eds., New Trends in Basement Membrane Research, pp. 59–67 (R. Timpl et al., "Macromolecular Organization of Type IV Collagen"), Raven Press, N.Y. (1982).
U. Schwartz–Magdolen et al., *FEBS Letters* 208: 203 (1986).
M. Kurkinen et al, *J. Biol. Chem.* 259: 5915 (1984).
J. Kyte and R. F. Doolittle, *J. Mol. Biol.* 157: 105 (1982).
W. Babel et al., *Eur. J. Biochem.* 143: 545 (1984).
J. M. Stewart and J. D. Young, in *Solid Phase Peptide Synthesis*, Pierce Chemical Company (publ.), Rockford, Ill. (2d ed., 1984).
R. M. Hewick et al., *J. Biol. Chem.* 256: 7990 (1981).
E. C. Tsilibary et al., *J. Cell. Biol.* 103: 2467–2473 (1986).
H. E. Kambic et al., *Chem. & Eng. News* (Apr. 14, 1986).
I. Oberbaumer et al., *Eur. J. Biochem.* 147: 217–224 (1985).
T. Pihlajaniemi et al., *J. Biol. Chem.* 260: 7681–7687 (1985).
M. Aumailley et al., *J. Cell Biol.* 103: 1569 (1986).
S. P. Sugrue, *J. Biol. Chem.* 262: 3338 (1987).
A. S. Charonis et al., *J. Cell Biol.*, 100: 1848 (1985).
F. Misselwitz et al., *Bulletin of Experimental Biology and Medicine* 98(9): 1274 (1985).
M. D. Pierschbacher et al., *Nature* 309: 30 (1984).
E. C. Tsilibary et al., *J. Biol. Chem.* 263: 4302–4308 (1988).

*Primary Examiner*—David M. Naff
*Attorney, Agent, or Firm*—Merchant, Gould, Smith, Edell, Welter & Schmidt

[57] ABSTRACT

A polypeptide which can bind heparin and promote cellular adhesion is provided, which consists essentially of a polypeptide having a formula selected from the group consisting of:
met-phe-lys-lys-pro-thr-pro-ser-thr-leu-lys-ala-gly-glu-leu-arg,
thr-ala-gly-ser-cyś-leu-arg-lys-phe-ser-thr met,
asn-pro-leu-cys-pro-pro-gly-thr-lys-ile-leu,
and mixtures thereof.

Medical devices such as prosthetic implants, percutaneous devices, bandages and cell culture substrates coated with the polypeptide composition are also provided.

5 Claims, 12 Drawing Sheets

```
        10         20         30         40         50         60         70
SVDHGFLVTR HSQTTDDPLC PPGTKILYGH YSLLYVQGNE RAHGQDLGTA GSCLRKFSTM PFLFCNINNV 80         90        100        110        120        130        140
CNFASRNDYS YWLSTPEPMP MSMAPISGDN IRPFISRCAV CEAPAMVMAV HSQTIQIPQC PNGWSSLWIG 150        160        170        180        190        200        210
YSFVMHTSAG AEGSGQALAS PGSCLEEFRS APFIECHGRG TCNYYANAYS FWLATIERSE MFKKPTPSTL

220
KAGELRTHVS RCQVCMRRT
```

POLYPEPTIDES FOR ADHERING CELLS TO A SUBSTRATE

Government Support

This invention was made with the support of Grant No. AM32660, from the National Institutes of Health. The Government has certain rights in the invention.

This application is a division of application Ser. No. 07/648,190, filed Jan. 31, 1991, now U.S. Pat. No. 5,059,425, which is a division of application Ser. No. 07/397,012, filed Aug. 22, 1989, now U.S. Pat. No. 5,007,925, which is a division of application Ser. No. 07/106,858, filed Oct. 8, 1987, now U.S. Pat. No. 4,876,332.

BACKGROUND OF THE INVENTION

Figure 1:
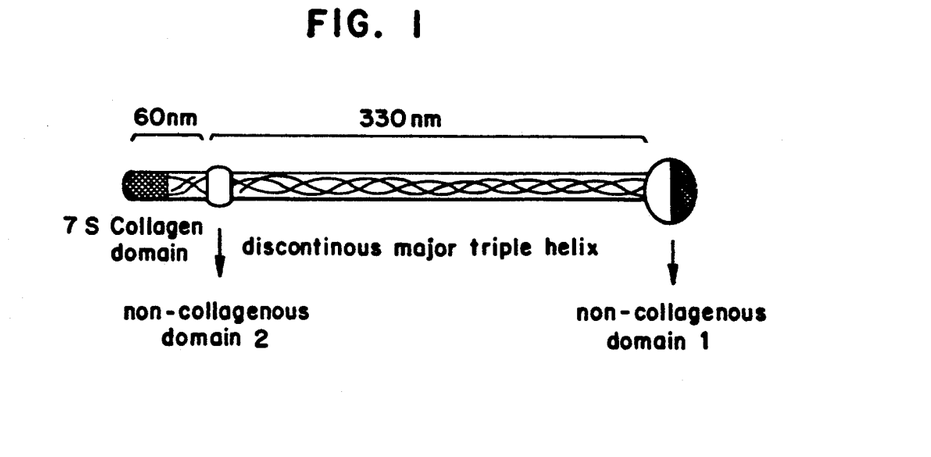
FIG. 1 is a diagrammatic representation of the type IV collagen molecule. The length of the two triple helical segments is indicated on the top. Black areas are those sites involved in the interaction with other type IV collagen molecules.

Type IV collagen is a distinctive glycoprotein which occurs almost exclusively in basement membranes. It differs from the other types of collagen, which are found mainly in interstitial connective tissue, with regard to several structural properties. See *New Trends in Basement Membrane Research*, K. Kuehn et al., eds., Raven Press, NY (1982) at pages 59-67. It has a molecular weight (MW) of about 500,000 and consists of three polypeptide chains: two α1 (MW 185,000) chains and one α2 (MW 170,000) chain. Type IV collagen has two major domains: a large, globular, non-collagenous, NC1 domain and another major triple-helical, collagenous domain. The latter domain is often interrupted by short, non-collagenous sequences. The amino acid sequence of this collagenous domain is only partially known; however, the sequence of both the α1- and α2- chains of the non-collagenous NC1 domain is known. See U. Schwartz-Magdolen et al., *FEBS Letters*, 208, 203 (1986), and references cited therein. A diagrammatic representation of the type IV collagen molecule is shown in FIG. 1. Apparently, type IV collagen is a very complex and multidomain protein with different biological activities residing in different domains.

Type IV collagen is an integral component of basement membranes because it self-assembles to higher forms which make up the supportive matrix of these structures. Various other macromolecular components of basement membranes are thought to assemble on this supportive framework. For example, laminin, nidogen and heparan sulfate proteoglycan have been reported to bind to type IV collagen. Laminin was observed to bind to two distinct sites along the length of the helix-rich, collagenous domain of type IV collagen. Nidogen and heparan sulfate proteoglycan were observed to bind specifically to the non-collagenous NC1 domain. Another property of type IV collagen is the ability to self-assemble by end-to-end and lateral associations, as mentioned hereinabove. The end-product of the polymerized structure is an irregular polygonal network. The NC1 domain is required for network formation because it binds along the length of the helix-rich domain and brings adjacent molecules together, thus initiating lateral assembly. In the absence of lateral assembly, only end-to-end associations occur and the network-structure cannot be formed.

An additional function of type IV collagen is the binding to various cell types via cell surface receptors [M. Kurkinen et al., *J. Biol. Chem.*, 259, 5915 (1984)]. M. Kurkinen et al. have reported that a major surface receptor protein with a molecular weight of 47,000 mediates this binding in the case of mouse embryo parietal endodermal cells.

The variety of functions attributed to type IV collagen indicates that this protein is an important reactant in many diverse and clinically important processes such as basement membrane assembly, cell migration, wound healing, tumor cell metastasis, diabetic microangiopathy, vascular hypertrophy due to hypertension and several kidney diseases. For example, Goodpasture's syndrome, a disease characterized by hemoptysis and hematuria due to alveolitis and nephritis, respectively, is associated with the presence of an antibody to the NC1 domain of type IV collagen in the serum of all Goodpasture's patients. Another hereditary kidney disease, Alport's familial nephritis is apparently due to a genetic defect of the NC1 domain of type IV collagen. Finally, in diabetes mellitus, intact type IV collagen, as well as the helix-rich domains, are chemically modified and functionally impaired by the increased amounts of glucose in the plasma and in the immediate vicinity of the basement membranes, i.e., in the extracellular matrix.

In order to better understand the pathophysiology of these processes at a molecular level, there is a need to try to assign each of the biological activities that type IV collagen exhibits to a specific sub-domain (i.e., NC1, helix-rich) or oligopeptide of type IV collagen. If this can be achieved, it may be possible to synthesize small peptides which can provide the basis for important pharmaceutical compositions.

BRIEF DESCRIPTION OF THE INVENTION

The present invention provides three polypeptides which formally represent fragments of the α1-NC1 chain of type IV collagen. The polypeptides, which can be prepared by conventional solid phase peptide synthesis, can be represented by the formulas:

met-phe-lys-lys-pro-thr-pro-ser-thr-leu-lys-ala-gly-glu-leu-arg  (I), thr-ala-gly-ser-cys-leu-arg-lys-phe-ser-thr-met  (II), and asn-pro-leu-cys-pro-pro-gly-thr-lys-ile-leu  (III).

Polypeptide I, (hereinafter "TS-1") formally represents amino acids 201-216 of the α1-NC1 domain, and can be represented by the single letter code: MFKKPTPSTLKAGELR. Polypeptide II formally represents isolated α1-NC1 amino acid residues 49-50, while polypeptide III formally represents isolated α1-NC1 amino acid residues 17-27. The single letter amino acid codes for these polypeptides are TAGSCLRKFSTM and NPLCPPGTKIL, respectively. For brevity, polypeptide II will be hereinafter designated as "TS-2" and polypeptide III will be designated as "TS-3". Some of their properties, such as hydropathy index, net charge and number of lysines, are shown in Table I, below.

TABLE I

| Peptide | Position in the α1-NC1 Chain (a.a. No. from the NH$_2$-terminus) | Hydropathy* Index | Net Charge | Number of Lysine Residues |
|---|---|---|---|---|
| TS-1 | 201-216 | −149 | +3 | 3 |
| TS-2 | 49-60 | +11 | +2 | 1 |

TABLE I-continued

| Peptide | Position in the α1-NCl Chain (a.a. No. from the NH₂-terminus) | Hydro- pathy* Index | Net Charge | Number of Lysine Residues |
| --- | --- | --- | --- | --- |
| TS-3 | 17–27 | <26 | 0 | 1 |

*Kyte and Doolittle, J. Mol. Biol., 157, 105 (1982).

These synthetic polypeptides were assayed for bioactivity and TS-2 and TS-3 were found to (a) bind to type IV collagen and to the isolated NCl domain thereof (TS-2 only), (b) bind to heparin, and (c) to inhibit the binding of heparin to type IV collagen. TS-1, TS-2 and TS-3 promote the adhesion of aortic endothelial cells and bind to melanoma cells (TS-3 only). Therefore, it is believed that TS-1, TS-2 and TS-3 may be useful to (a) promote wound healing and implant acceptance, (b) promote cellular attachment to culture substrata and/or (c) inhibit the metastasis of malignant cells. Due to the difference in the spectra of biological activities exhibited by polypeptides TS-1, TS-2 and TS-3, mixtures of TS-1, TS-2 and TS-3 are also within the scope of the invention.

Furthermore, since it is expected that further digestion/hydrolysis of polypeptides TS-2 and TS-3 in vitro or in vivo will yield fragments of substantially equivalent bioactivity, such lower molecular weight polypeptides are considered to be within the scope of the present invention.

DETAILED DESCRIPTION OF THE INVENTION

Figure 2:
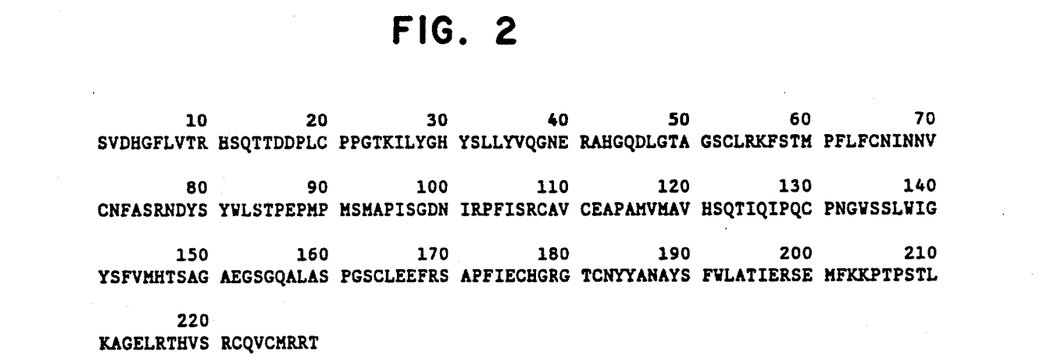
FIG. 2 depicts the complete amino acid sequence of the α1-NCl chain of type IV collagen, in single letter amino acid code.

The amino acid sequence of the helix-rich collagenous part of the α1 chain has been partially described by W. Babel et al., Eur. J. Biochem., 143, 545 (1984). The full sequence of the noncollagenous α1-NCl is shown in FIG. 2. The sequence information available on the globular NCl domain of the α1 chain was examined and the three polypeptides of the invention, designated TS-1, TS-2 and TS-3, were synthesized for further evaluation.

*Synthesis of Polypeptides* The polypeptides of the invention were synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Ill. (2d ed., 1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxy-carbonyl (BOC) group is used to protect the free amino group of the amino acid. This protecting group is removed with 25% trifluoroacetic acid (TCA) in dichloromethane (DCM). The newly exposed amino group is converted to the free base by 10% triethylamine (TEA) in DCM. The next BOC-protected amino acid is then coupled to the free amine of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized at the University of Minnesota Microchemical facility by the use of a Beckman System 990 Peptide synthesizer.

Following synthesis of a blocked polypeptide on the resin, the resin-bound polypeptide is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0M acetic acid, followed by lyophilization of the extract.

Lyophilized crude polypeptides are purified by preparative high performance liquid chromatography (HPLC) by reverse phase technique on a C-18 column. A typical elution gradient is 0% to 60% acetonitrile with 0.1% TFA in H₂O. Absorbance of the eluant is monitored at 220 nm, and fractions are collected and lyophilized.

Characterization of the purified polypeptide is by amino acid analysis. The polypeptides are first hydrolyzed anaerobically for 24 hours at 110° C. at 6M HCl (constant boiling) or in 4N methanesulfonic acid, when cysteine or tryptophane are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

The invention will be further described by reference to the following detailed examples.

EXAMPLE 1

Liquid Phase Collagen Binding Assay

The ability of these peptides to bind to type IV collagen and to the NC1 domain was evaluated by a variety of approaches. In the first place, network formation by prewarmed intact type IV collagen was examined via the technique of rotary shadowing at the electron microscopic level. Table II lists the permutations which were tested and statistically evaluated (by counting the number of fields which contained irregular polygonal networks).

TABLE II

| Run | Material |
|-----|----------|
| (1) | type IV collagen alone (control). |
| (2) | type IV collagen and albumin (BSA; another control). |
| (3) | type IV collagen and isolated NC1 domain (control NC1).* |
| (4) | type IV collagen and diabetically modified or glucosylated NC1 domain. |
| (5) | type IV collagen and peptide TS-1. |
| (6) | type IV collagen and peptide TS-2. |
| (7) | type IV collagen and peptide TS-3. |

*The NC1 domain was isolated by collagenase treatment of murine, EHS-derived, purified type IV collagen, as described by Tsilibary et al. (J. Cell. Biol., 103, 2467-2473 (1986)).

Figure 3A:
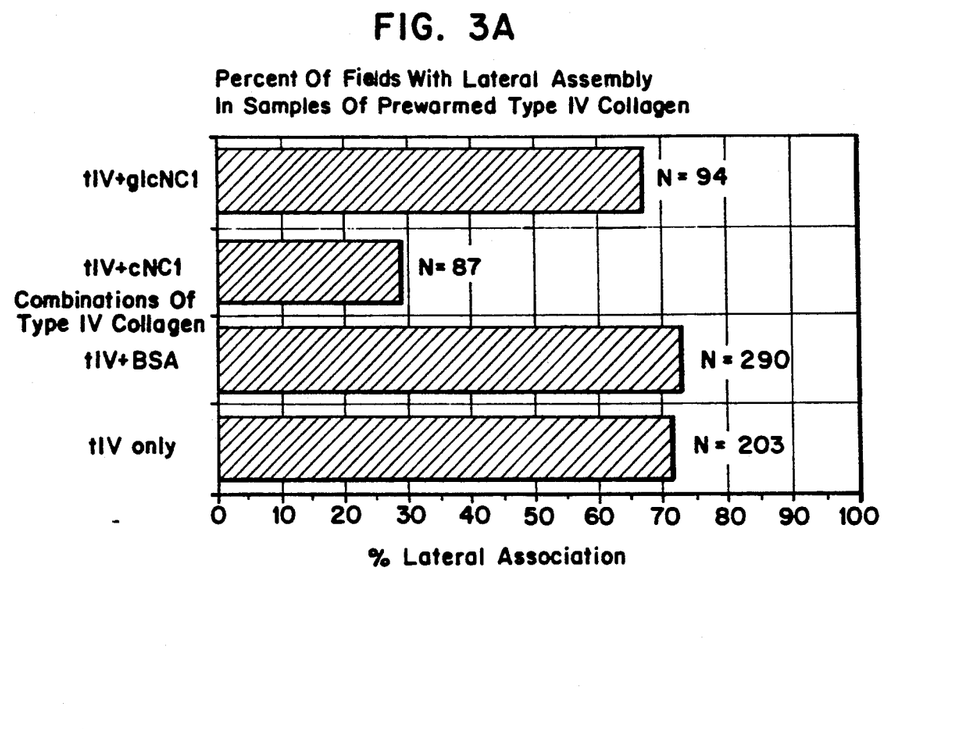
FIGS. 3A and 3B are graphical depictions of the effect of the polypeptides of the invention on type IV collagen network formation.
Figure 3B:
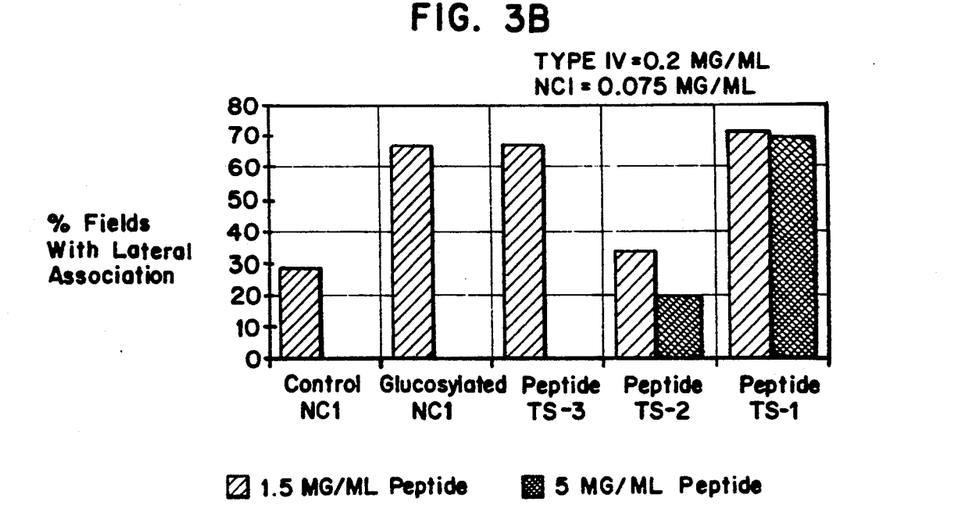

The comparative assembly data obtained from permutations 1-4 are shown in FIG. 3A. The comparative assembly data obtained from permutations 5-7 are shown in FIG. 3B, which also shows the results obtained using type IV collagen with control NC1 domain and with glucosylated NC1 domain.

The data summarized on Tables 3A and 3B confirm that: (a) control NC1 domain binds to type IV collagen and competes for network formation; and (b) diabetically modified or glucosylated NC1 domain cannot bind to type IV collagen because it cannot compete for network formation. Specifically, it was observed that polypeptide TS-2 can mimic the effect of intact, control NC1 domain, since it can effectively prevent network formation. The other two peptides, TS-1 and TS-3, do not have any effect on the assembly of type IV collagen (FIG. 3B).

EXAMPLE 2

Solid Phase Collagen Binding Assay

Figure 4:
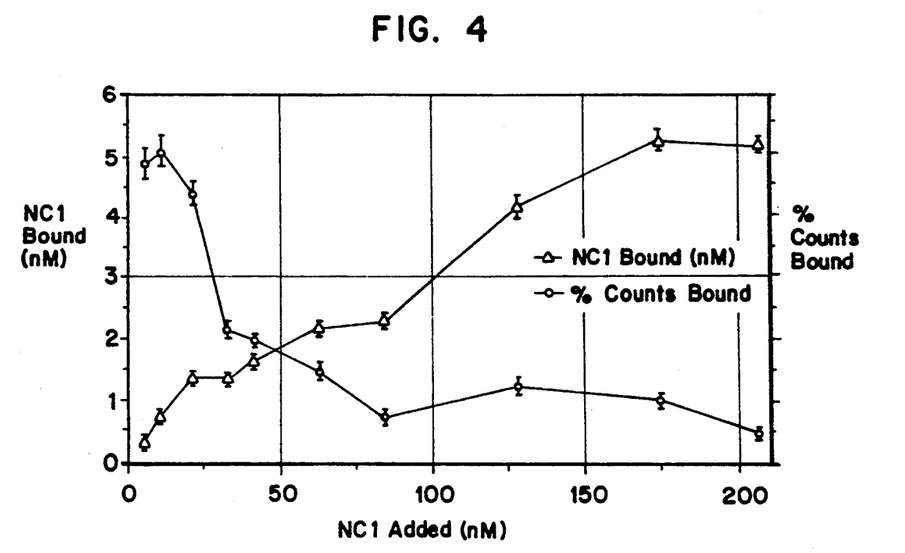
FIG. 4 is a graphical depiction of the binding of intact NCl domain to type IV collagen.

The binding of the intact NC1 domain and polypeptides TS-2 and TS-3 to type IV collagen was also examined by solid phase binding assays. Type IV collagen was coated onto a plastic surface and the binding of isolated NC1 domain was examined by adding increasing concentrations of $^{125}$I-labelled NC1 domain (isolated from purified type IV collagen by treatment with collagenase). These data are shown in FIG. 4. It was observed that increasing amounts of $^{125}$I-NC1 bound to type IV collagen as the concentration of NC1 added was increased, until a plateau was reached, indicating that all available sites for binding to the NC1 domain were occupied. This saturable binding of $^{125}$I-NC1 to type IV collagen was specific since it could be competed for by an excess of unlabelled NC1 domain (FIG. 4).

Figure 5:
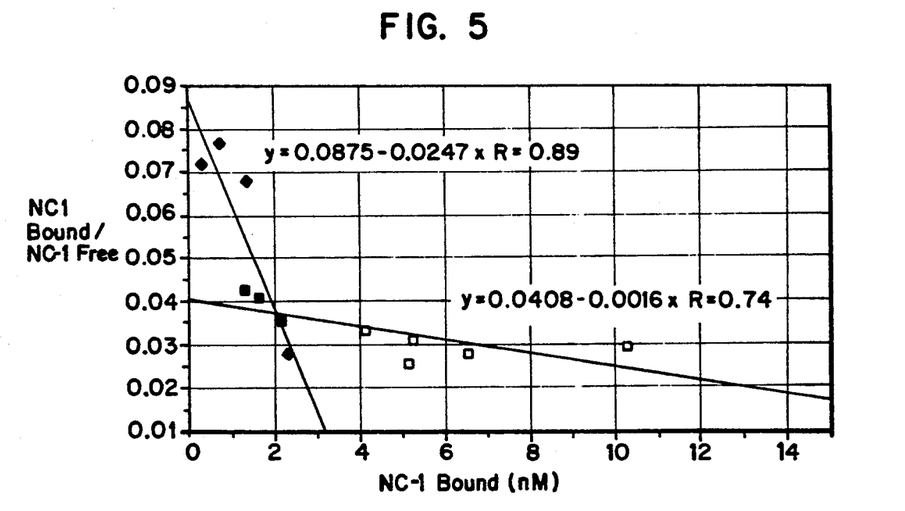
FIG. 5 is a Scatchard plot of the binding of intact NCl domain in solution to type IV collagen, which has been immobilized on a plastic surface.

Analysis of the affinity of the binding of NC1 domain to type IV collagen by a Scatchard plot indicated two classes of binding sites with two different binding constants were present (FIG. 5). The two binding constants were 40 nM and 330 nM, respectively.

Figure 6:
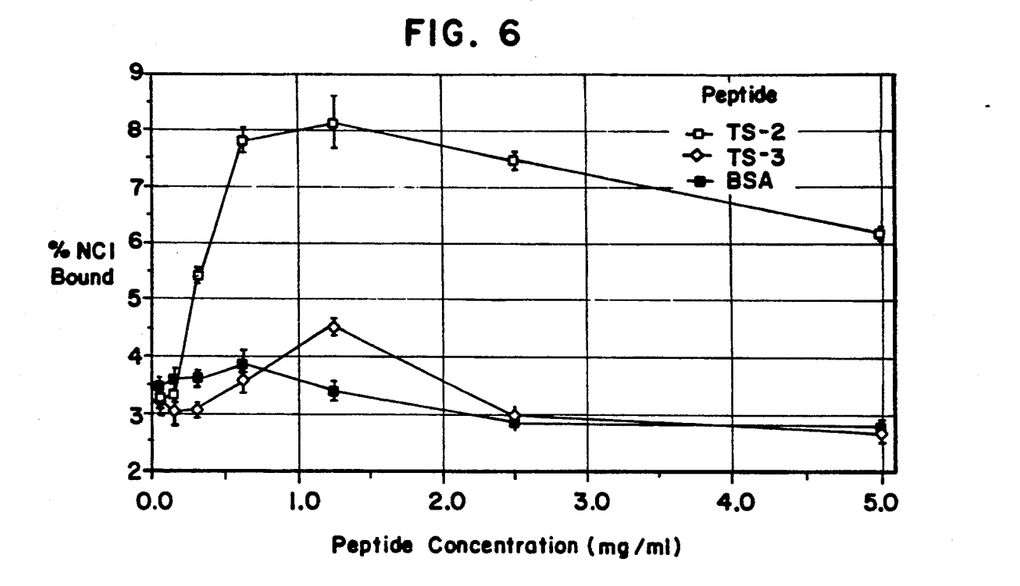
FIG. 6 is a graphical depiction of the binding of polypeptides TS-2 and TS-3 to intact NCl domain and to type IV collagen.

Type IV collagen in PBS (10 μg/ml, 50 λ) was added to plastic wells and allowed to bind to the plastic surface by incubation overnight at 4° C. Subsequently, $^{125}$I-labelled NC1 domain was allowed to interact with the immobilized type IV collagen in the presence of BSA, peptide TS-2 or peptide TS-3. When peptide TS-3 was added in solutions of $^{125}$I-NC1, it did not have any effect on the subsequent binding of $^{125}$I-NC1 to type IV collagen (FIG. 6). The presence of peptide TS-2 in solutions of $^{125}$I-NC1 caused a dramatic increase of the binding of $^{125}$I-NC1 to type IV collagen until a plateau was reached (FIG. 6). These data indicate that peptide TS-2 can bind to type IV collagen and also to the isolated NC1 domain. This double binding ability of the peptide would account for the observed increase in binding of the NC1 domain to type IV collagen when higher concentrations of peptide TS-2 are used.

EXAMPLE 3

Heparin Binding Assays

Figure 7:
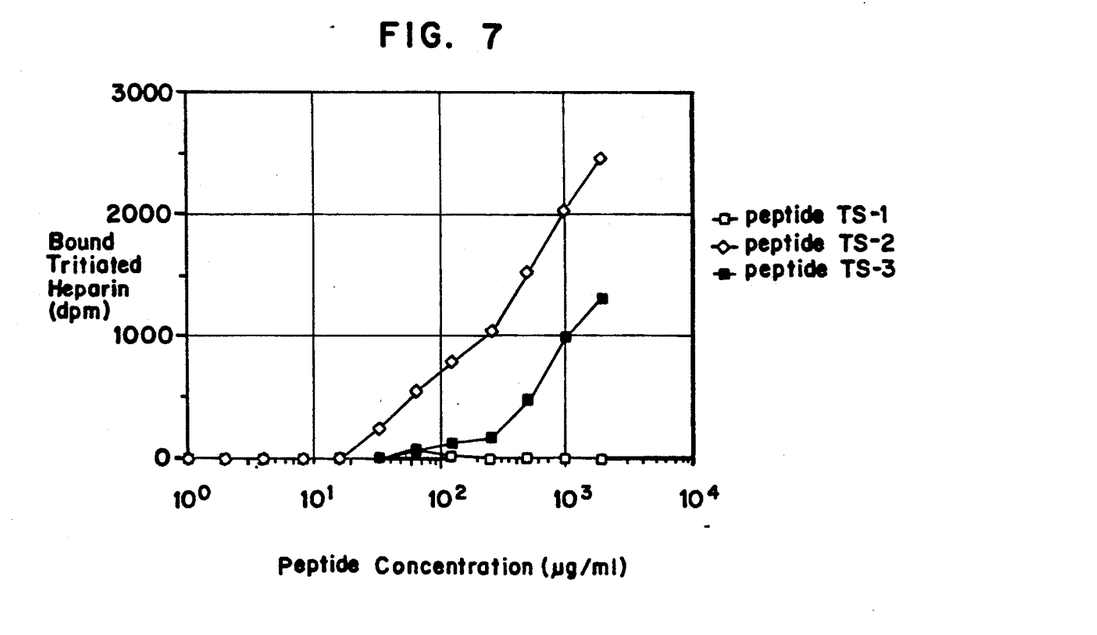
FIG. 7 is a graphical depiction of the binding of the polypeptides of the invention to heparin.

In order to test the ability of the present polypeptides to bind to heparin, a solution of 2 mg/ml of each polypeptide in 50 mM ammonium bicarbonate (pH 7.8) was prepared and then serially diluted 1:1 in the same buffer to produce concentrations from 2 mg/ml to 1 μg/ml. One hundred μl from each dilution were incubated with $^3$H-heparin (50,000 dpm/ml) for two hours at 37° C. and the mixtures were then added to nitrocellulose-coated wells. The wells were then washed in 10 mM Tris-HCl pH 8.0 (4×, 2 min each time). The amount of $^3$H-heparin bound to each peptide at each dilution is shown in FIG. 7. The results of this experiment indicate that peptides TS-2 and TS-3 bind to heparin (TS-2 to a greater extent than TS-3), whereas TS-1 does not interact with heparin.

Figure 8:
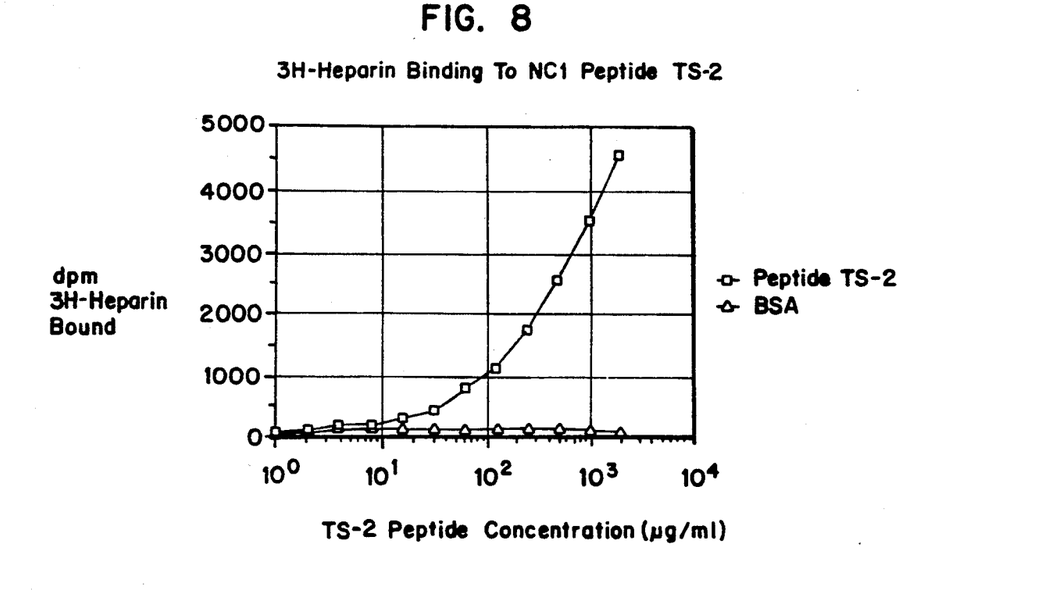
FIGS. 8–9 are graphical depictions of the ability of polypeptides TS-2 and TS-3, respectively, to bind to immobilized heparin.
Figure 9:
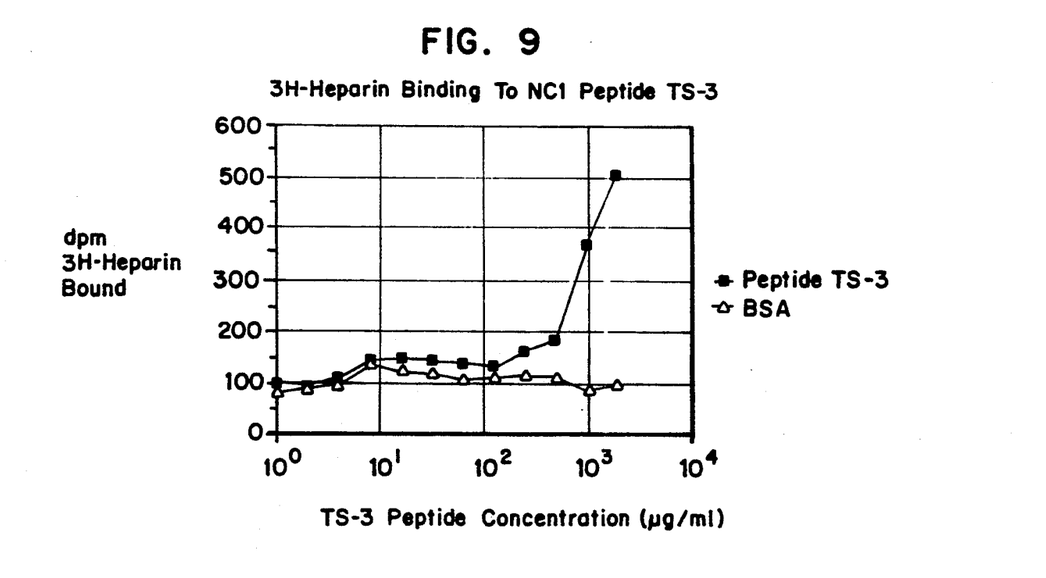

The ability of the present polypeptides to interact with heparin when coated on 96-well plastic plates was evaluated. Stock solutions of the polypeptides at a maximum concentration of 2 mg/ml were prepared and serially diluted in phosphate-buffered saline (PBS)+NaN$_3$, producing final concentrations from 2 mg/ml to 1 μg/ml. Fifty μl from each dilution were coated on the 96-well plates and left to dry overnight at 28° C. Then, the wells were treated for two hours with 2 mg/ml BSA in order to minimize nonspecific ligand binding. $^3$H-heparin was added (50,000 dpm/well) and the mixture incubated for two hours. After extensive washing, the $^3$H-heparin bound at each peptide concentration was removed with sodium dodecyl sulfate (SDS) and counted in a scintillation counter. The results shown in FIG. 8 indicate that peptide TS-2 binds heparin strongly. Peptide TS-3 also binds heparin, but less extensively (FIG. 9). Peptide TS-1 does not bind heparin above background (BSA) values.

Figure 10:
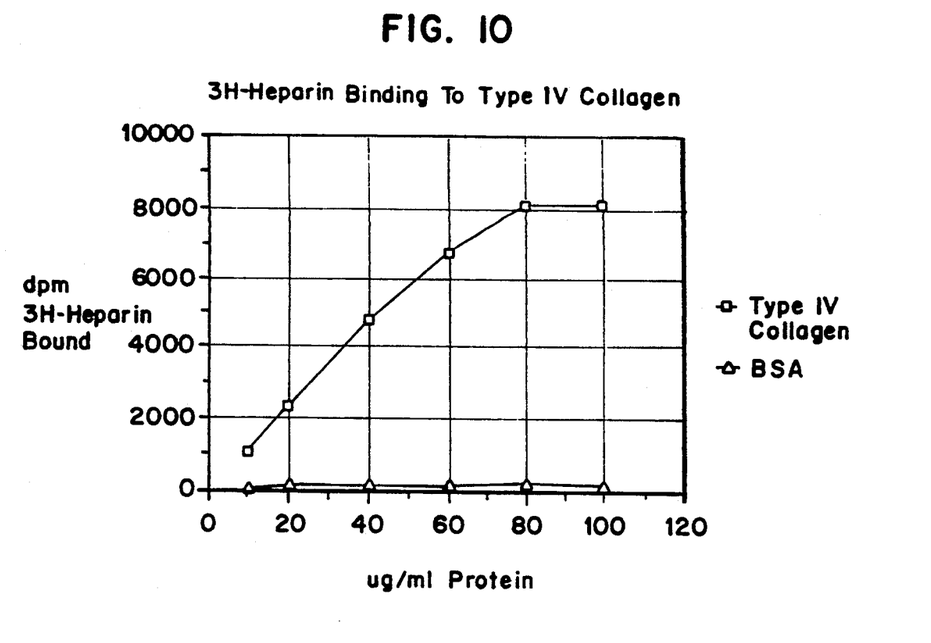
FIGS. 10–11 are graphical depictions of the binding of ³H-heparin to type IV collagen and to NCl domain, respectively.
Figure 11:
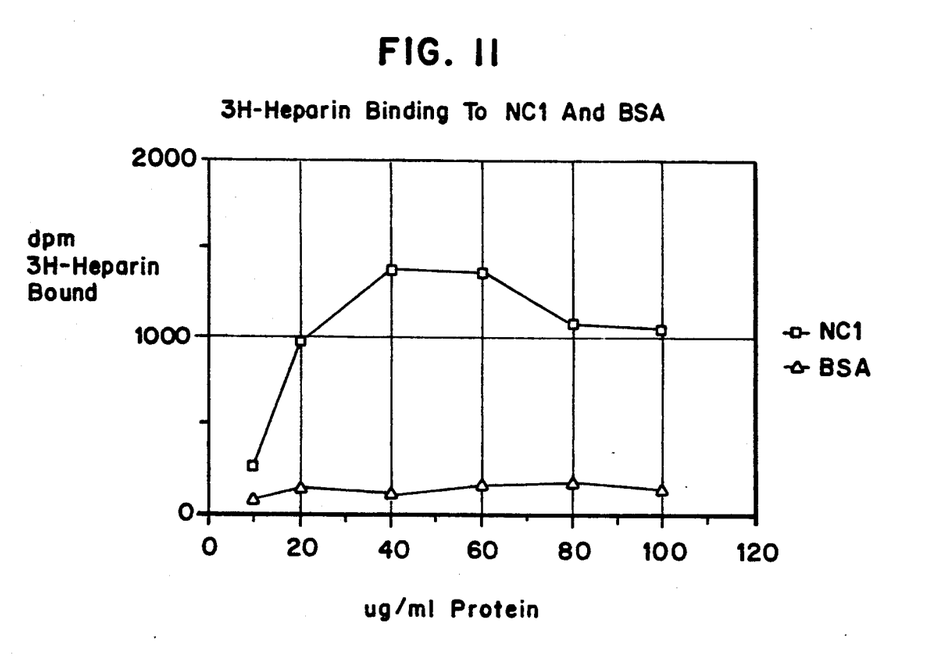

It was then established that $^3$H-heparin binds both to intact, native type IV collagen and to the isolated NCl domain. FIGS. 10 and 11 show the binding of a constant amount of $^3$H-heparin (85,000 dpm) to increasing concentrations of type IV collagen and the NCl domain, respectively. A saturable binding is observed in both cases. Type IV collagen binds 5–6 times more $^3$H-heparin than does the NCl domain.

Figure 12:
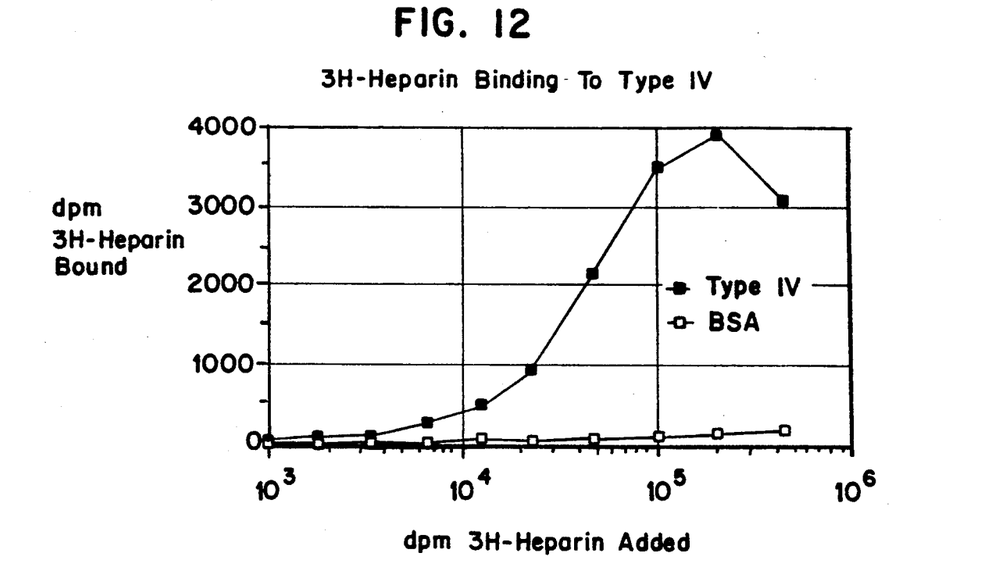
FIGS. 12–13 are graphical depictions of the binding of increasing concentrations of ³H-heparin to constant amount of type IV collagen and NCl domain, respectively.
Figure 13:
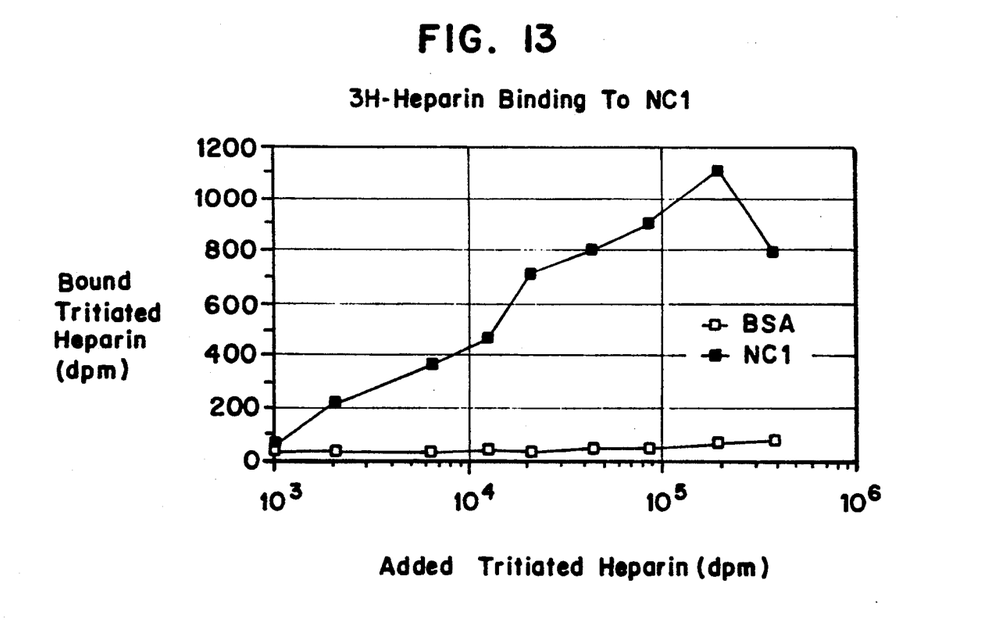

Next, the binding of increasing concentrations of $^3$H-heparin to a constant amount of type IV collagen (3 $\mu$g) and an equimolar amount of the NCl domain (1 $\mu$g) was tested. Again, a saturable binding of $^3$H-heparin to type IV collagen (FIG. 12) and the NCl domain (FIG. 13) was observed. In this type of experiment, approximately 4 times more $^3$H-heparin bound to type IV collagen than to the NCl domain. These data indicate that at least two binding sites for heparin exist in type IV collagen: one in the NCl domain and the other(s) in the helix-rich part of the molecule.

Next, solutions of the three peptides of the invention (not absorbed to plastic) were screened for ability to inhibit the binding of heparin to intact, native type IV collagen coated on plastic. This experimental approach is intended to obviate problems due to any differential coating of peptides in heparin binding assays.

Type IV collagen at 60 $\mu$g/ml in PBS+0.1% Triton-X was coated on 96-well plates (use of 50 $\mu$l or 3 $\mu$g of laminin per well), dried overnight at 28° C. and then the wells were coated with 2 gm/ml bovine serum albumin (BSA) in PBS. Peptides at various dilutions ranging from 2 mg/ml to 1 $\mu$g/ml were co-incubated with a standard amount of $^3$H-heparin (30,000 dpm/well) for two hours and the mixture was then transferred to the type IV collagen-coated plates and allowed to incubate for another two hours. After extensive washing, the radioactivity retained in each well was counted.

Figure 14A:
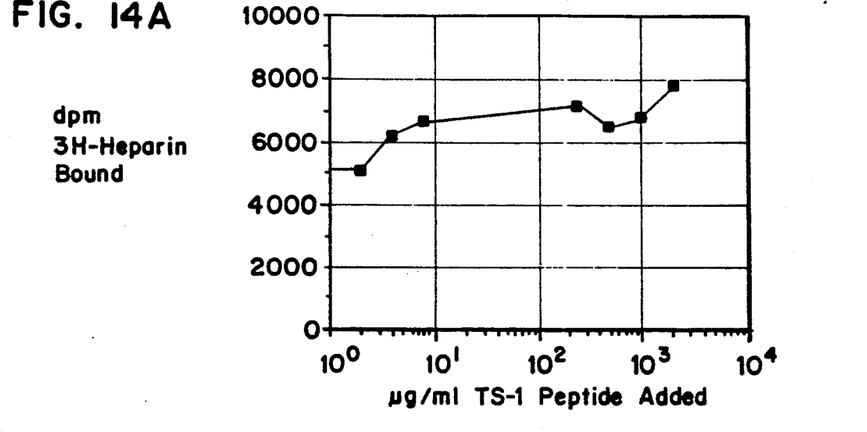
FIGS. 14A–C are graphical depictions of the inhibition of ³H-heparin binding to type IV collagen by polypeptides TS-1, TS-2 and TS-3, respectively.
Figure 14B:
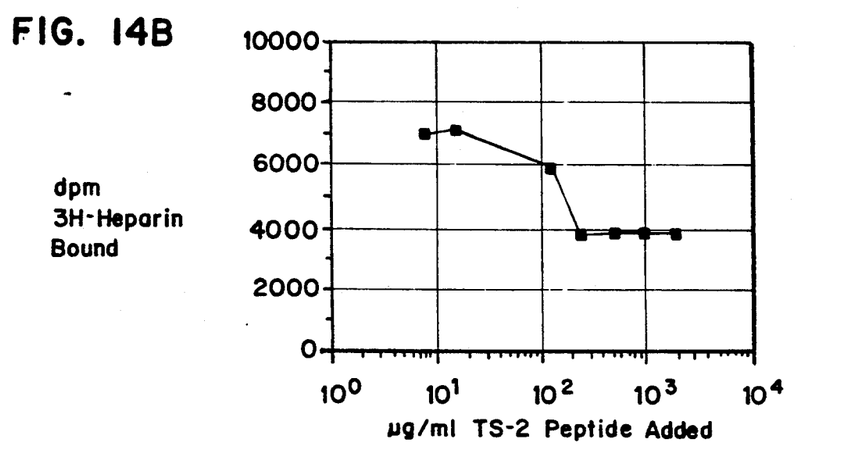
Figure 14C:
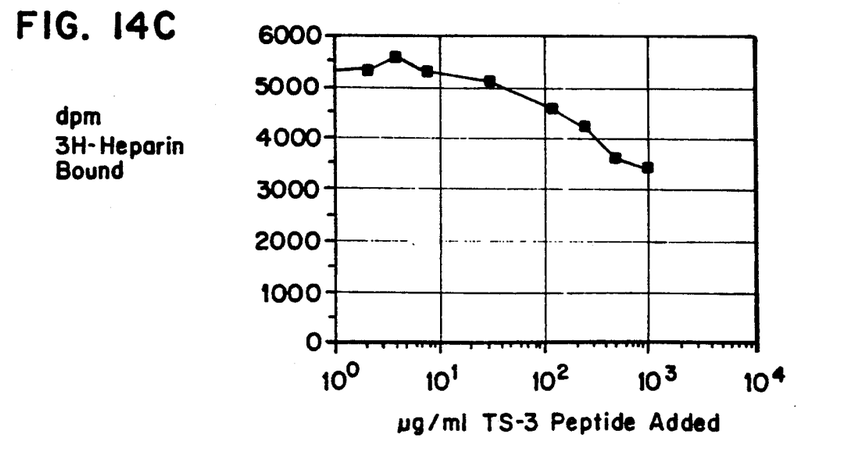

The results shown in FIG. 14 indicate that peptides TS-2 (FIG. 14B) and TS-3 (FIG. 14C) interact with heparin in this assay, since they both exhibited an about 43% inhibition of the binding of $^3$H-heparin to collagen at the highest concentration tested. However, peptide TS-2 was able to significantly inhibit the binding of $^3$H-heparin to type IV collagen at lower concentrations than TS-3, and therefore, bound to heparin with higher affinity. TS-1 does not interact with heparin by this assay (FIG. 14A).

Peptides TS-2 and TS-3 were able to bind to heparin in all the assays which were performed. It is interesting that peptide TS-2 binds both to heparin and to type IV collagen. These data indicate the presence of more than one binding site in this peptide. Therefore, it is possible that binding of heparin to one binding site of this peptide competes for the binding of the peptide to type IV collagen. Also, this peptide could be used to link heparin and type IV collagen together, as well as to bind them to various biomaterials.

EXAMPLE 4

Cell Adhesion Assays

These assays were performed with the following cell lines: aortic endothelial cells, metastatic melanoma murine (M$_4$) cells, normal rat fibroblasts, MM fibroscarcoma cells, C6 glioma cells and breast carcinoma (A431) cells. Cell binding assays were performed in the same way for each cell line and the three peptides of the invention, TS-1, TS-2 and TS-3 were individually assayed in each case for cell adhesion.

Adhesion was tested in each case, using a 96-well microtiter plates absorbed with four different amounts (0.5; 5; 50; and 500 $\mu$g/ml, 100 $\lambda$/well) of peptides TS-1, TS-2, TS-3 and BSA. Cultures of cells which were 60–80% confluent were metabolically labelled for 24 hours by the addition of 3 mCi of $^3$H-thymidine. On the day of the assay, the cells were harvested by trypsinization, the trypsin was inhibited by the addition of serum and the cells were washed free of this mixture and resuspended in DMEM. The cells were adjusted to a concentration of $6 \times 10^5$/ml and 100 $\mu$l of this cell suspension was added to the wells. The assay mixture was then incubated at 37° C. for 90 min. At the end of the incubation, the wells were washed with warm PBS containing 10 MM Ca++ and the adherent population was solubilized with 0.5M NaOH containing 1% sodium dodecyl sulfate. The solubilized cells were then quantitated using a liquid scintillation counter. Each determination was done in triplicate.

A. Aortic Endothelial Cells

Aortic endothelial cells were obtained from bovine aortas by treatment with collagenase and were frozen at −196° C. until use. These cells were cultured in primary cultures in the presence of DMEM and 10% fetal calf serum at 37° C. in a humid atmosphere. When aortic endothelial cells were about 70% confluent, they were released from the tissue culture plastic by trypsin and then were added in suspension to the wells of 96-well plates coated with the following peptides: (a) TS-1, (b) TS-2 and (c) TS-3, in the concentrations described above.

Figure 15:
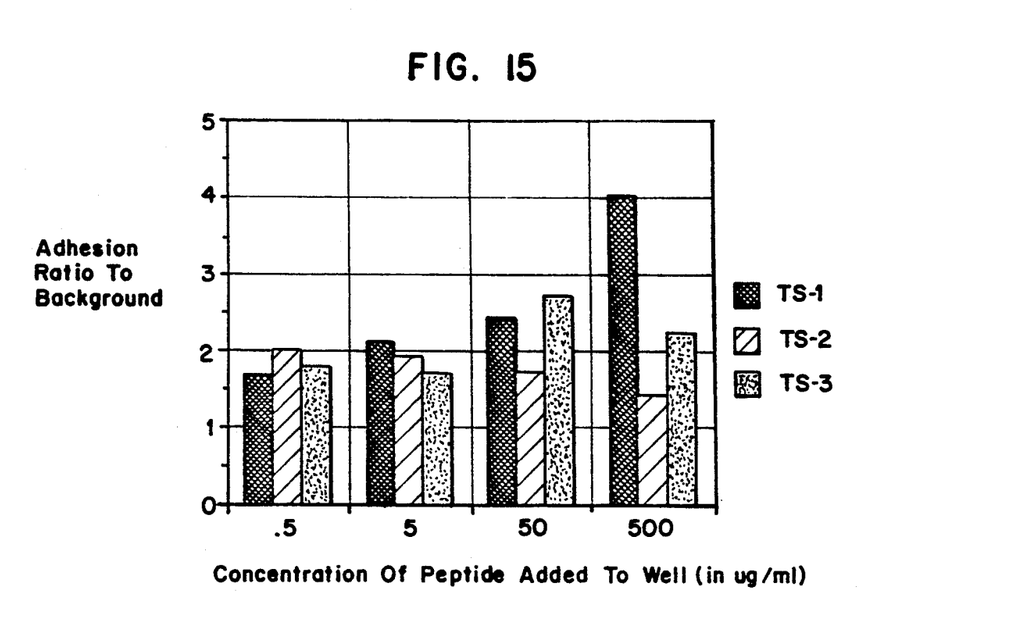
FIG. 15 is a graphical depiction of the binding of the present peptides to aortic endothelial cells.

The cells were metabolically labelled with 3.0 mCi of $^3$H-thymidine for 24 hours prior to the assay. After trypsinization, the cells were allowed to attach for a 90-minute incubation period in the peptide-coated wells. After extensive washing, the radioactivity associated with each well was measured and used as an index of cell attachment (expressed as percent adherent). The data summarized on FIG. 15 shows that peptide TS-1 was the most potent in causing the adhesion of aortic endothelial cells, followed by peptides TS-2 and TS-3, respectively. In FIG. 15, the background values due to BSA binding were subtracted.

B. Metastatic Melanoma Cells

Highly metastatic melanoma cells, K1735M4, were originally provided by Dr. I. J. Fidler of Houston, Tex. When the cells were recieved, a large number of early passage cells were propagated and frozen in liquid nitrogen. The tumor cells are usually cultured in vitro for no longer than six weeks. Following this period, the cells are discarded and new cells withdrawn from storage for use in further in vitro or in vivo experiments. This precaution is taken to minimize phenotypic drift that can occur as a result of continuous in vitro passage. The cells were cultured in Dulbecco's Modified Eagle's Medium (DMEM) containing 5% heat inactivated fetal calf serum. The cultures were grown in 37° C. incubators under a humidified atmosphere containing 5% CO$_2$. Cells were subcultured twice weekly by releasing cells gently from the flask, using 0.05% trypsin and 1 mM EDTA.

The melanoma cells were metabolically labelled in the same fashion as the endothelial cells described hereinabove, using 2 μCi/ml $^3$HTdR (tritiated thymidine). The labelled cells were harvested as described for the endothelial cells. The cell adhesion assay was indentical to that described hereinabove for the bovine aortic endothelial cell assay.

Figure 16:
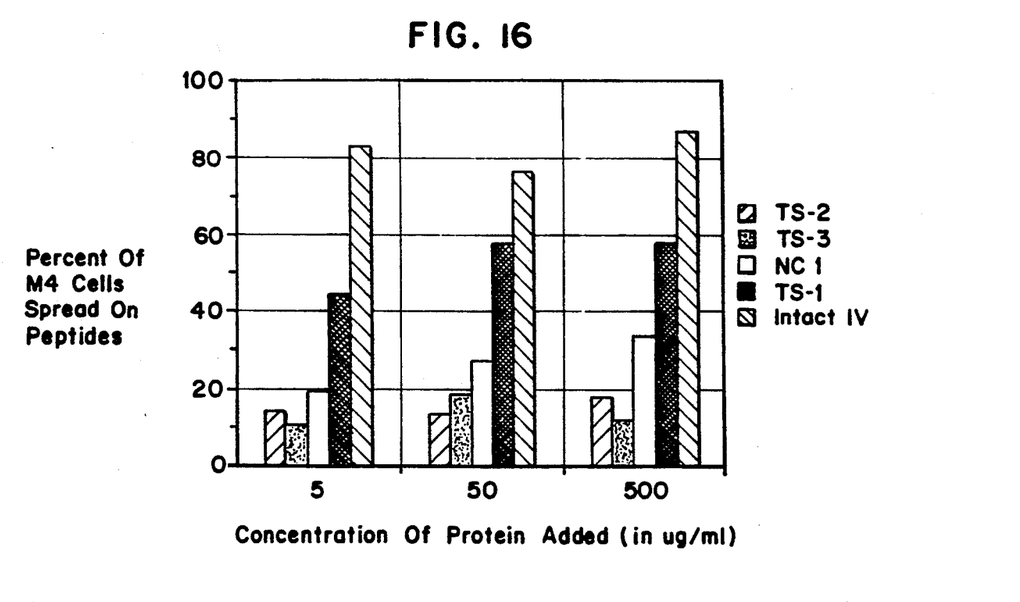
FIG. 16 is a graphical depiction of the binding of the present peptides to M₄ melanoma cells.

The data summarized in FIG. 16 demonstrates that peptides TS-1, TS-2 and TS-3 promote adhesion of M$_4$ cells. Peptide TS-1 was the most potent in this respect. In this figure, adhesion of M$_4$ cells to intact type IV collagen and isolated NCl domain is shown for comparison. Background adhesion to BSA has been substracted.

C. Normal Rat Fibroblasts

Figure 17:
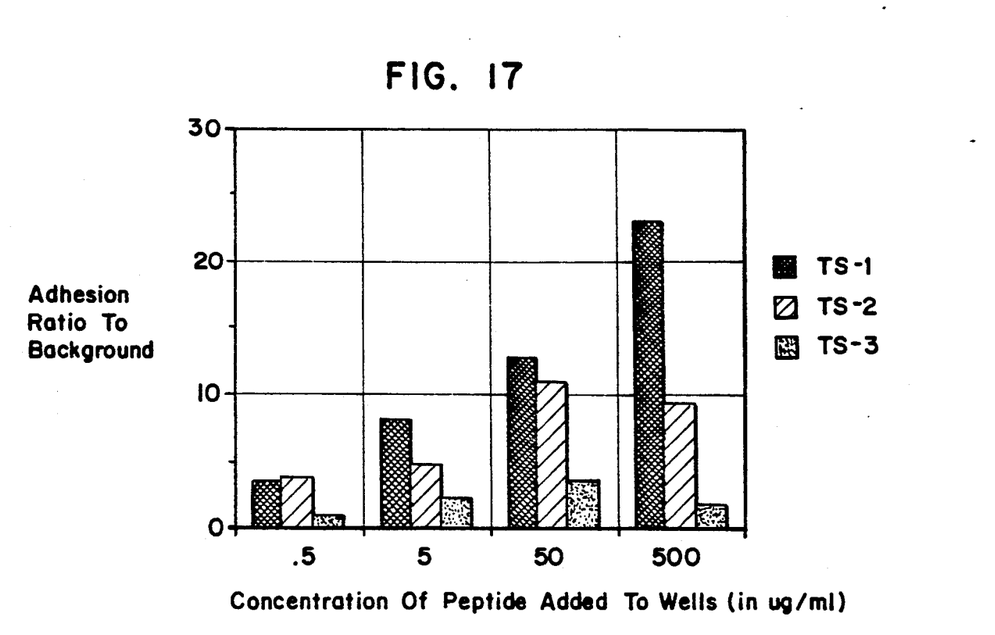
FIG. 17 is a graphical depiction of the binding of the present peptides to normal rat fibroblasts.

These cells were obtained from cultures of rat dermis explants in DMEM containing 10% fetal calf serum, in plastic wells. Under these conditions, fibroblasts migrated to the bottom of the plastic dish. When the cells were confluent, they were harvested by trypsinization and were then metabolically labelled, as described above, for the cell adhesion assay. FIG. 17 shows that peptide TS-1 was the most potent in promoting adhesion of these cells followed by peptides TS-2 and TS-3, which promoted adhesion of rat fibroblasts to a minimal extent. Background adhesion to BSA has been subtracted.

D. Isolation of and Cell Adhesion Assay for MM Fibro-sarcoma Cell Line

Figure 18:
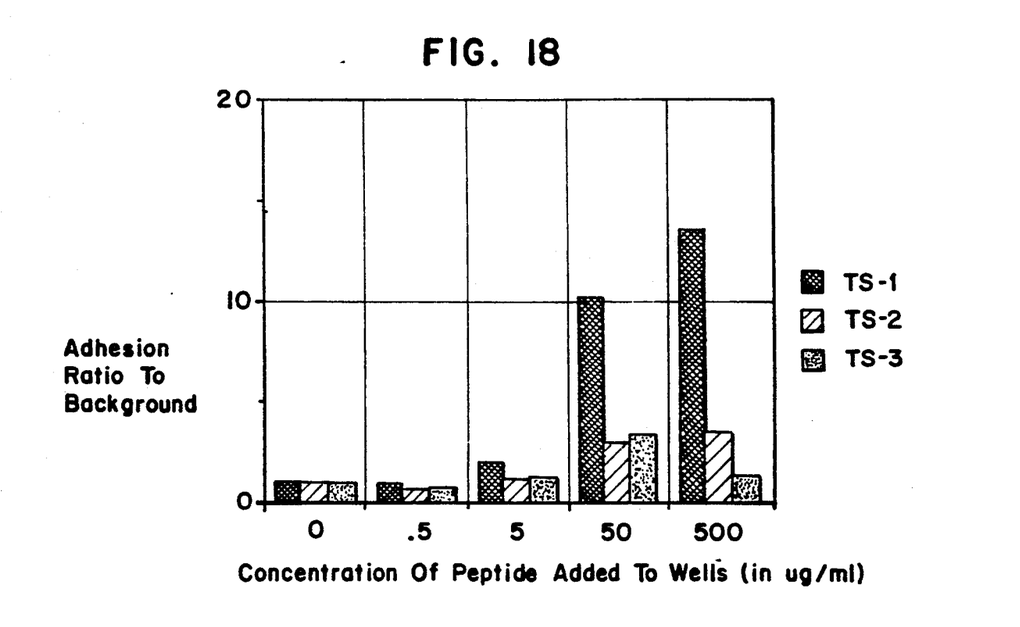
FIG. 18 is a graphical depiction of the binding of MM fibrosarcoma cells to peptides TS-1, TS-2 and TS-3.

Murine fibrosarcoma cells (uv-2237-MM) were originally provided by Dr. I. J. Fidler of Anderson Hospital, University of Texas Health Sciences Center, Houston, Tex. Culturing, labelling and harvesting techniques were as described in Part A. The results of this assay are summarized in FIG. 18. Background adhesion to BSA has been subtracted.

E. Isolation of and Cell Adhesion Assay for C6 Cell Line

Figure 19:
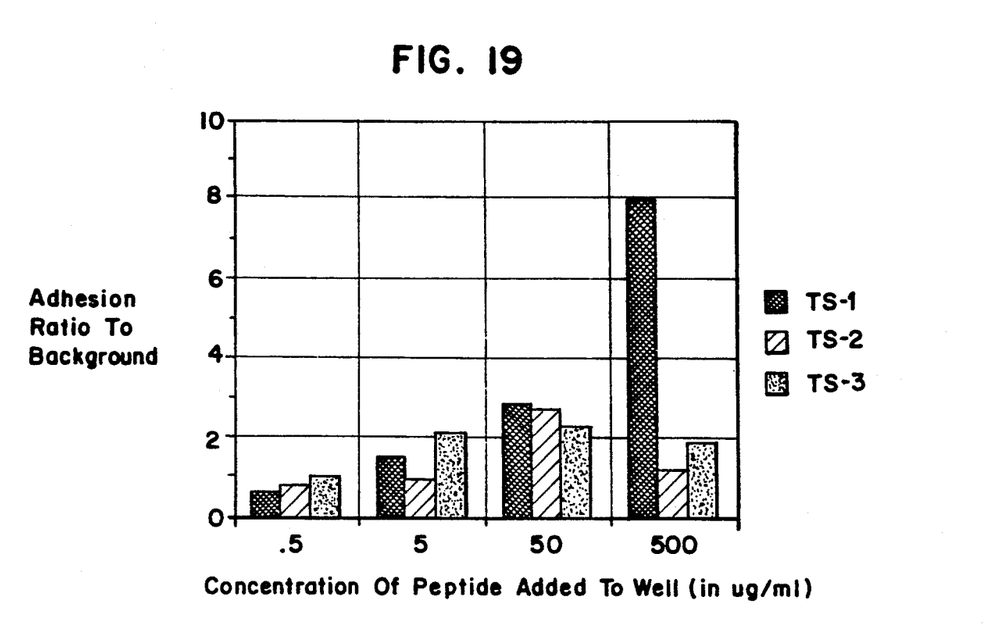
FIG. 19 is a graphical depiction of the binding of the present peptides to C6 glioma cells.

Rat C6 glioma cell line was purchased from the American Type Culture Collection (identification number CCL 107). Culturing techniques were as described in Part A. Labelling and harvesting techniques were as described above, under Example 4. The results of this assay are summarized in FIG. 19. Peptides TS-1, TS-2 and TS-3 promoted adhesion of C6 glioma cells. At the highest concentration, peptide TS-1 was the most potent in promoting adhesion. Background adhesion to BSA has been subtracted.

F. A431 Breast Carcinoma Cells

Figure 20:
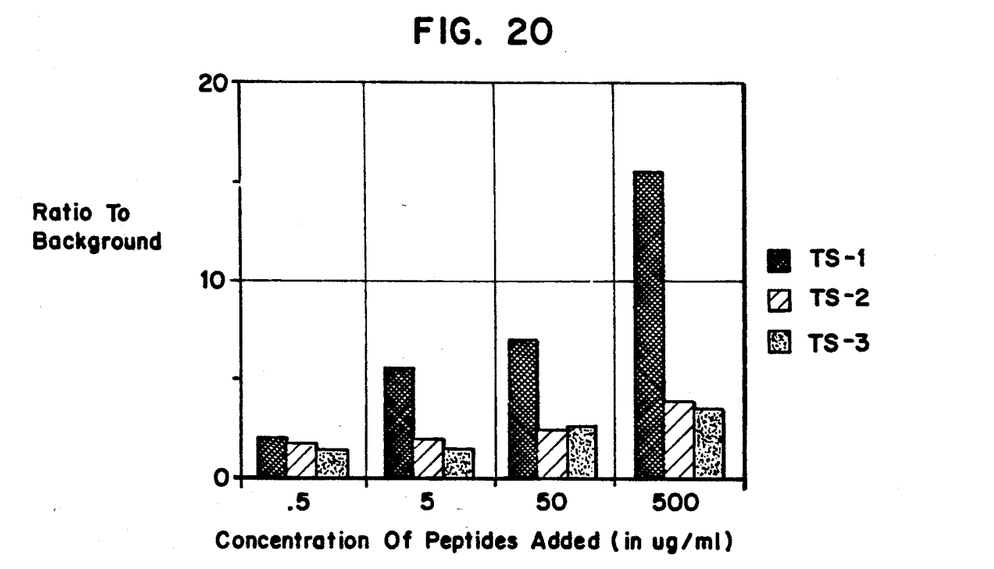
FIG. 20 is a graphical depiction of the binding of peptides TS-1, TS-2 and TS-3 to A431 carcinoma cells.

A431 cells were purchased from the American Type Culture Collection. Culturing, labelling and harvesting techniques have been described above (see methodology under Example 4, and Part A). The results of this assay are summarized in FIG. 20. Background adhesion to BSA has been subtracted.

Figure 21:
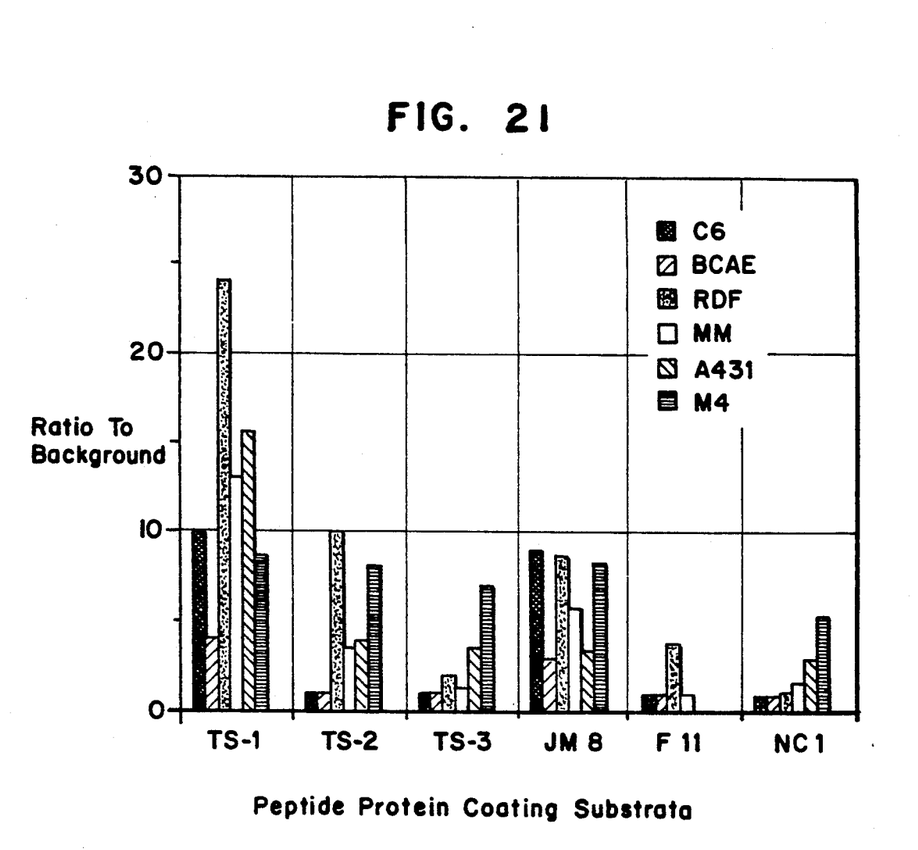
FIG. 21 is a composite depicting the binding of the present peptides to various cell lines.

FIG. 21 summarizes the data with respect to the adhesion of the above-mentioned peptides TS-1, TS-2 and TS-3 to the previously described cell lines. Two other irrelevant peptides were also used: JM-8, as a positive control (a peptide derived from the sequence of fibronectin, which is known to promote cell adhesion) and F-11 (a peptide derived from the sequence of the $\beta_1$ chain of laminin, which does not promote cell adhesion and which was used as a negative control). Adhesion to isolated domain NCl is also shown for comparison. Background adhesion to BSA has been subtracted.

In summary, peptide TS-1 promotes adhesion of aortic endothelial cells, metastatic carcinoma M$_4$ cells, normal rat fibroblasts, MM fibrosarcoma cells, C6.glioma cells and A431 breast carcinoma cells. Peptide TS-2 binds (a) to type IV collagen, (b) to heparin and (c) promotes adhesion of the above-mentioned cell lines. Peptide TS-3 (a) binds to heparin and (b) promotes adhesion of the above-mentioned cell lines.

A number of practical applications for polypeptides TS-1, TS-2 and TS-3 can be envisioned. Such applications include the promotion of the healing of wounds caused by the placement of natural or synthetic substrata within the body. Such synthetic substrata can include artificial vessels, intraocular contact lenses, hip replacement implants and the like, where cell adhesion is an important factor in the acceptance of the synthetic implant by normal host tissue.

As described in U.S. Pat. No. 4,578,079, medical devices can be designed making use of these polypeptides to attract cells to the surface in vivo or even to promote the growing of a desired cell type on a particular surface prior to grafting. An example of such an approach is the induction of endothelial cell growth on a prosthetic device such as a blood vessel or vascular graft, which is generally woven or knitted from a synthetic resin such as nitrocellulose, expanded polytetrafluoroethylene or polyester fiber, particularly Dacron TM (polyethylene tetephthalate) fiber. Devices intended for cardiac insertion include temporary left ventricular assist devices, heart valves, intraortic balloon pumps and artificial hearts. Such devices are preferably formed from synthetic resins such as polyether-type polyurethane elastomers (Cardiothane TM, Kontron) or from vulcanized polyolefin rubbers (Hexsyn TM, Goodyear).

Most types of cells are attracted to collagen and to the present polypeptides, but endothelial cells, epithelial cells and fibroblastic cells in particular may be strongly attracted to the present polypeptides. The latter point indicates the potential usefulness of these defined polypeptides in coating a patch graft or the like for aiding wound closure and healing following an accident or surgery.

In such cases, it may be advantageous to couple the peptide to a biological molecule, such as collagen, a glycosaminoglycan or a proteoglycan. Collagens, proteoglycans and glycosaminoglycans are major components of connective tissues and basement membranes. In some cases, prosthetic devices formed entirely or in part from naturally-occurring tissues instead of synthetic polymers are used. One example is the use of porcine heart valves to replace defective human heart valves. Such artificial valves can also comprise human dura matter or bovine pericardium. Another example is the use of bovine arteries as vascular grafts.

It may be useful to coat surfaces of these biological substrata with the present polypeptides, in order to modify the cellular response, in vivo, thus improving the therapeutic outcome. This can be achieved by a variety of methods known to the art, e.g., by direct binding of the polypeptides to the target surfaces based on the affinities described hereinabove, or by the covalently bonding the polypeptides to the substrate using various crosslinking reactions or reagents. For a review of the use of synthetic resins and biomaterials in prosthetic devices, see *Chem. & Eng. News* (Apr. 14, 1986) at pages 30–48, the disclosure of which is incorporated by reference herein.

It is also indicative of their value in coating surfaces of a prosthetic device which is intended to serve as a temporary or semipermanent entry into the body, e.g., into a blood vessel or into the peritoneal cavity, sometimes referred to as a percutaneous device. Such devices include controlled drug delivery reservoirs or infusion pumps.

Also, polypeptides TS-1, TS-2 and TS-3 can be used to promote endothelial, fibroblast or epithelial cell adhesion to naturally occurring or artificial substrata intended for use in vitro. For example, a culture substrate such as the wells of a microtiter plate or the medium-contacting surface of microporous fibers or beads, can be coated with the cell-attachment polypeptides. This can obviate the use of fibronectin in the medium, thus providing better defined conditions for the culture as well as better reproducibility.

As one example of commercial use of cell-attachment surfaces, Cytodex ™ particles, manufactured by Pharmacia, are coated with gelatin, making it possible to grow the same number of adherent cells in a much smaller volume of medium than would be possible in dishes. The activity of these beads is generally dependent upon the use of fibronectin in the growth medium and the present polypeptides are expected to provide an improved, chemically-defined coating for such purposes. Other surfaces or materials may be coated to enhance attachment, such as glass, agarose, synthetic resins or long-chain polysaccharides.

Finally, TS-1, TS-2 and TS-3 can be used to coat the surface of medical devices intended for external application of attachment to the body. Such devices include "bandages", which term is also intended to refer to wound packs and dressings, which can comprise surfaces formed from absorbent cellulosic fibers, from synthetic fibers or from mixtures thereof. These surfaces can be coated with amounts of TS-1, TS-2 and/or TS-3 effective to promote cellular growth, wound healing, graft attachment and the like.

The invention has been described with reference to various specific and preferred embodiments and techniques. However, it should be understood that many variations and modifications may be made while remaining within the spirit and scope of the invention.

What is claimed is:

1. A cell culture substrate having a surface coated with a polypeptide having a formula selected from the group consisting of:
   met-phe-lys-lys-pro-thr-pro-ser-thr-leu-lys-ala-gly-glu-leu-arg,
   thr-ala-gly-ser-cys-leu-arg-lys-phe-ser-thr-met,
   asn-pro-leu-cys-pro-pro-gly-thr-lys-ile-leu,
   and mixtures thereof.

2. The cell culture substrate of claim 1 wherein said surface is made of a synthetic resin.

3. The cell culture substrate of claim 1 wherein said surface constitutes a portion of a bead.

4. The cell culture medium of claim 1 wherein said surface constitutes a portion of a microporous fiber.

5. The cell culture medium of claim 1 wherein said surface constitutes the wells of a microtiter plate.

* * * * *

UNITED STATES PATENT AND TRADEMARK OFFICE
CERTIFICATE OF CORRECTION

PATENT NO.   :   5,242,826
DATED        :   September 7, 1993
INVENTOR(S)  :   Tsilibary et al.

It is certified that error appears in the above-identified patent and that said Letters Patent is hereby corrected as shown below:

Column 3, line 6, "<26" should be -- -26--

Column 3, line 62, "amount" should be --amounts--

Column 9, line 29, "Fibro-sarcoma" should be --Fibrosarcoma--

Column 12, line 1, "of" should be --or--

Signed and Sealed this

Fifth Day of July, 1994

BRUCE LEHMAN

Attest:

Attesting Officer

Commissioner of Patents and Trademarks